US00PP34913P2

(12) United States Plant Patent
Petruschke

(10) Patent No.: US PP34,913 P2
(45) Date of Patent: Jan. 17, 2023

(54) PEAR TREE ROOTSTOCK NAMED 'VIRUTHERM-1'

(50) Latin Name: ***Pyrus* x *michauxii***
Varietal Denomination: ViruTherm-1

(71) Applicant: Consortium Deutscher Baumschulen GmbH, Ellerbek (DE)

(72) Inventor: Michael Petruschke, Bietigheim-Bissingen (DE)

(73) Assignee: Consortium Deutscher Baumschulen GmbH, Ellerbek (DE)

( * ) Notice: Subject to any disclaimer, the term of this patent is extended or adjusted under 35 U.S.C. 154(b) by 0 days.

(21) Appl. No.: 17/692,897

(22) Filed: Mar. 11, 2022

(51) Int. Cl.
*A01H 5/08* (2018.01)
*A01H 6/74* (2018.01)

(52) U.S. Cl.
USPC ..... Plt./179

(58) Field of Classification Search
USPC ..... Plt./176, 179
See application file for complete search history.

(56) References Cited

U.S. PATENT DOCUMENTS

PP5,573 P * 10/1985 Brooks ..... Plt./36

* cited by examiner

*Primary Examiner* — Susan McCormick Ewoldt
(74) *Attorney, Agent, or Firm* — The Webb Law Firm

(57) ABSTRACT

A new and distinct variety of pear tree rootstock tree that exhibits resistance to *Candidatus* Phytoplasma pyri, no suckering, and is compatible with all pear varieties.

3 Drawing Sheets

Botanical classification: *Pyrus* x *michauxii.*
Varietal denomination: 'ViruTherm-1'.

BACKGROUND OF THE INVENTION

The present invention comprises a new and distinct variety of pear tree that is solely used as a rootstock and known by the varietal name 'ViruTherm-1'. The new variety was discovered and selected by the breeder in a cultivated field trial environment in Bavendorf, Germany in 2014 as a naturally occurring whole plant mutation amongst a population of unpatented and unnamed pear tree plants. As such, the exact parentage is unknown. The new variety was selected and first asexually reproduced by in-vitro propagation in Cesena, Italy in 2019.

When compared to *Pyrus communis* variety named 'Kirchensaller Mostbirne' (unpatented), both varieties are stable in the ground and do not exhibit calcium chlorosis. However, 'ViruTherm-1' exhibits more elongated leaves, much fewer thorns, and weaker growth when compared to 'Kirchensaller Mostbirne'. Further, the new variety exhibits resistance to *Candidatus* Phytoplasma pyri—a distinguishing characteristic of the new variety from other pear tree varieties known to the breeder.

The new variety has not been evaluated under all possible environmental conditions. The phenotype may vary with variations in environment without a change in the genotype of the plant. The new variety has been trial and field tested and has been found to retain its distinctive characteristics and remain true to type through successive asexual propagations.

DESCRIPTION OF THE DRAWINGS

The accompanying photographic drawings illustrate the new variety at approximately 1 year of age, with the color being as nearly true as possible with color illustrations of this type.

DETAILED BOTANICAL DESCRIPTION

Figure 1:
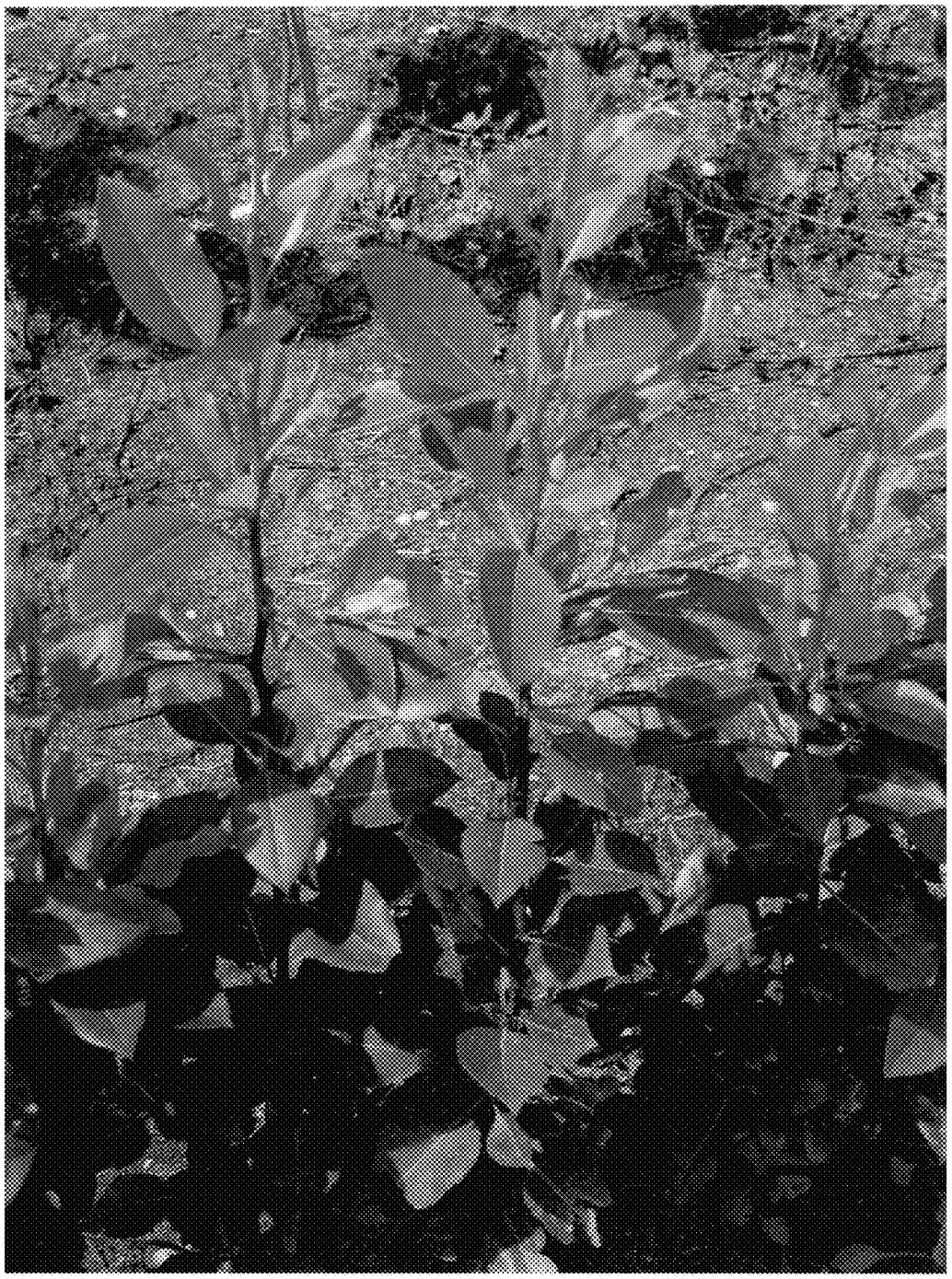
FIG. 1 illustrates a close-up view of plants of 'ViruTherm-1'.
Figure 2:
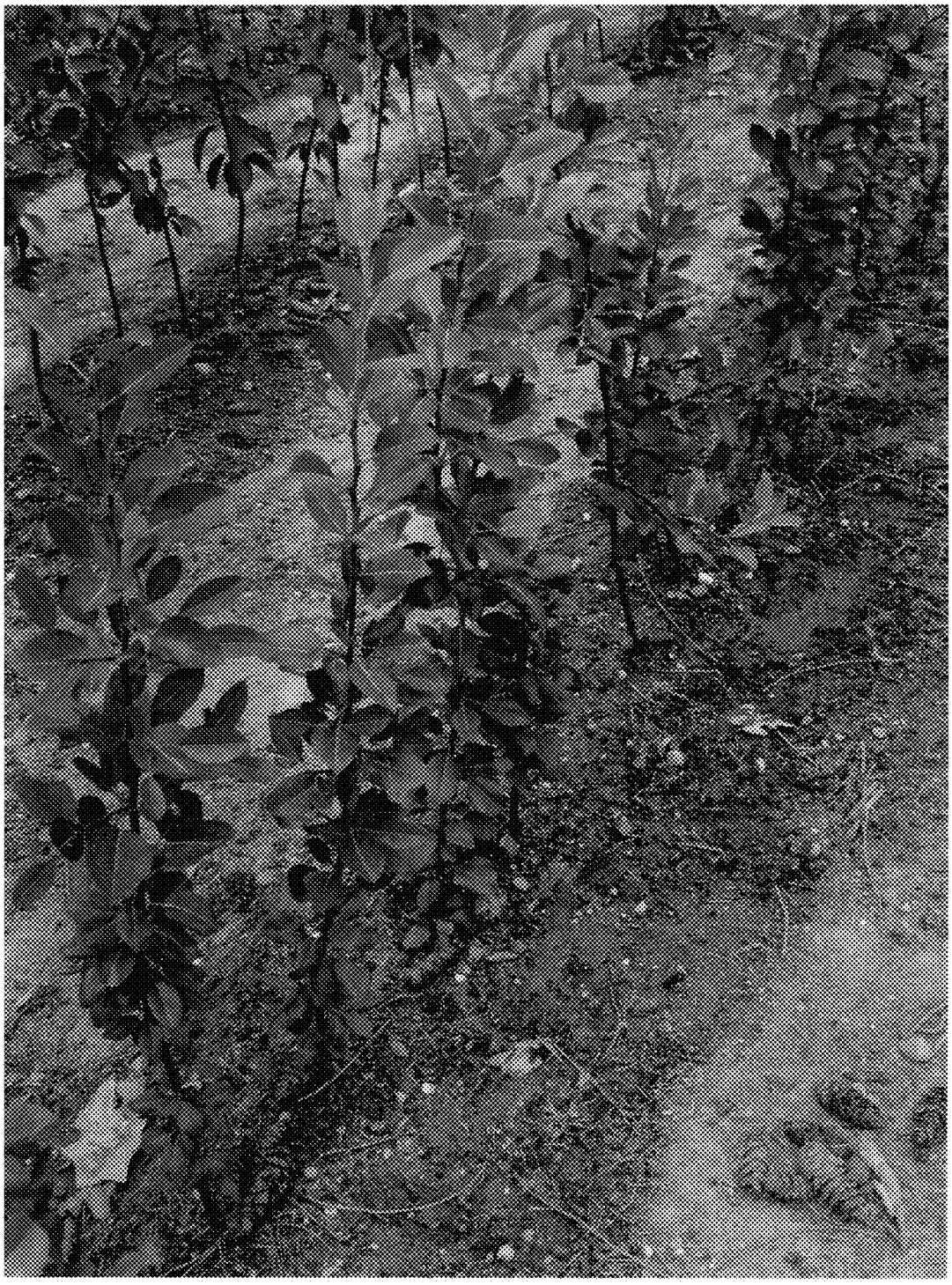
FIG. 2 illustrates multiple plants of 'ViruTherm-1'.
Figure 3:
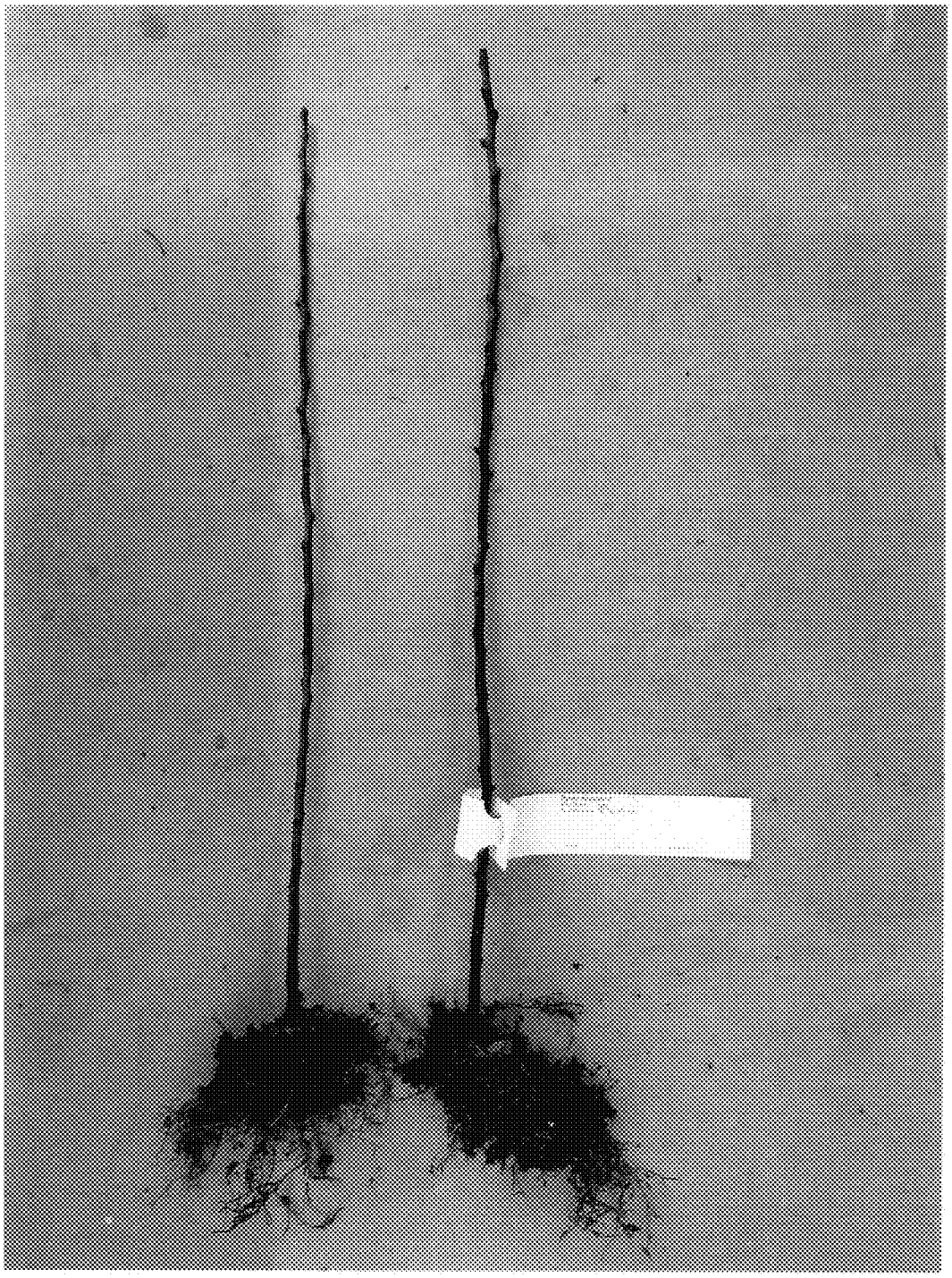
FIG. 3 illustrates the roots of 'ViruTherm-1'.

The following detailed description sets forth the characteristics of the new cultivar at approximately 1 year of age. The data which defines these characteristics were collected as a result of asexual reproductions carried out in Ellerbek, Germany on field grown plants under standard growing conditions and taken under natural light. Color descriptions are provided using X11 Color Names and their corresponding HEX Color Codes, accessed in October of 2022 via https://www.farb-tabelle.de/de/farbtabelle.htm.

ROOTSTOCK

Height: 120.0 cm.
Thickness: 8.0-10.0 mm.
Vigor: Moderate.
Tree habit: Upright.
Wood color: SaddleBrown, HEX #8B4513.
Use: Solely as a rootstock.
Vegetative shoots:
- *Overall habit.*—Upright.
- *Growth habit.*—Straight.
- *Surface texture.*—Smooth, with no pubescence present.
- *Internode length.*—Less than or equal to 5.0 mm.
- *Lenticels.*—Quantity: 20 per/cm. Length: 0.5 mm. Width: 0.2 mm. Shape: Rounded. Color: Khaki1, HEX #FFF68F.
- *Bud.*—Length: 5.0 mm. Width: 4.0 mm. Apex shape: Pointed. Color: Sienna4, HEX #8B4726.

Petiole:
- *Shape.*—Straight.
- *Length.*—1.5 cm.
- *Diameter.*—0.1 cm.
- *Color.*—Khaki2, HEX #EEE685.

Leaves:

*Arrangement*.—Alternate, spiral.

*Length*.—4.5 cm.

*Width*.—3.0 cm.

*Form*.—Elliptic-oval.

*Apex*.—Pointed.

*Base*.—Oval.

*Margin*.—Serrate.

*Texture*.—Upper surface: Slightly rough. Lower surface: Smooth.

*Color*.—Upper surface (young and mature leaves): OliveDrab3, HEX #9ACD32. Lower surface (young and mature leaves): LightGreen, HEX #90EE90.

*Venation*.—Type: Pinnate, alternate. Color: LightGreen, HEX #90EE90.

Stipules:

*Length*.—Less than or equal to 3.0 mm.

*Diameter*.—0.2 mm.

*Margin*.—Entire.

*Color*.—LightGreen, HEX #90EE90.

Multiplication ability:

*Layering*.—Very difficult.

*Hardwood cuttings*.—Very difficult.

*Softwood cuttings*.—Very difficult.

Pathogen/disease resistance/susceptibility: Resistant to *Candidatus* Phytoplasma pyri.

Pest resistance/susceptibility: Nothing unusual noted to date.

Average bud burst timing: Middle of March in Ellerbek, Germany.

Heat tolerance: To 40° C.

Cold tolerance: To −25° C.

Drought tolerance: Very good.

Rootstock performance:

*Root sprouts* (*suckering*).—None.

*Anchorage*.—Stable.

*Compatibility*.—Very good with all pear varieties.

*Vigor*.—Medium to strong.

Flowers/fruit: Not observed to date.

I claim:

1. A new and distinct variety of pear tree rootstock plant named 'ViruTherm-1', as is herein illustrated and described.

* * * * *